United States Patent
Hashimoto et al.

(10) Patent No.: US 7,741,235 B2
(45) Date of Patent: Jun. 22, 2010

(54) COMPOSITE SHEET AND ABSORBENT ARTICLE USING THE SAME

(75) Inventors: Tatsuya Hashimoto, Kagawa (JP); Hirotomo Mukai, Kagawa (JP); Satoshi Mitsuno, Kagawa (JP); Tomoko Tsuji, Kagawa (JP); Kenichi Akaki, Kagawa (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 195 days.

(21) Appl. No.: 11/945,545

(22) Filed: Nov. 27, 2007

(65) Prior Publication Data

US 2008/0124996 A1   May 29, 2008

(30) Foreign Application Priority Data

Nov. 28, 2006  (JP) .............................. 2006-319608

(51) Int. Cl.
*B32B 5/26* (2006.01)
(52) U.S. Cl. .................... 442/381; 428/167; 428/170; 428/171; 428/180; 442/328; 442/329
(58) Field of Classification Search ................ 442/328, 442/329, 381; 428/167, 170, 171, 180, 156
See application file for complete search history.

(56) References Cited

U.S. PATENT DOCUMENTS

| 4,652,487 | A | | 3/1987 | Morman |
| 6,146,367 | A | * | 11/2000 | Otsubo et al. .......... 604/385.01 |
| 6,481,483 | B1 | * | 11/2002 | Kobayashi et al. .......... 156/462 |

FOREIGN PATENT DOCUMENTS

| JP | 2002-371456 | 12/2002 |
| JP | 2006-089907 | 4/2004 |

* cited by examiner

*Primary Examiner*—Norca L Torres-Velazquez
(74) *Attorney, Agent, or Firm*—Morrison & Foerster LLP

(57) ABSTRACT

A composite sheet that has a low basis weight and can inhibit adhesives from flowing out is provided. The composite sheet 1 according to the present invention is formed by bonding a stretchable nonwoven fabric 2 and a non-stretchable nonwoven fabric 3 to each other with adhesives 4. The stretchable nonwoven fabric 2 in an extended state is bonded to the non-stretchable sheet. The stretchable nonwoven fabric 2 has a plurality of strip-shaped non-dense regions 21 and a plurality of strip-shaped dense regions 22 formed on both its surfaces alternately and alternately in the transverse direction such that the dense regions 22 on one of the surfaces and the dense regions 22 on the other surface are not overlapped with each other. The stretchable nonwoven fabric 2 includes thermoplastic fibers that have been stretched at least partially and elastomer fibers.

7 Claims, 10 Drawing Sheets direction M

COMPOSITE SHEET AND ABSORBENT ARTICLE USING THE SAME

This application is based on and claims the benefit of priority from Japanese Patent Application No. 2006-319608, filed on 28 Nov. 2006, the content of which is incorporated herein by reference.

BACKGROUND OF THE INVENTION

1. Field of the Invention

The present invention relates to a composite sheet and an absorbent article using the composite sheet.

2. Related Art

Composite sheets having a plurality of nonwoven fabrics laminated with adhesives or the like have been conventionally used in various applications and have been subjected to various types of processing in accordance with the intended uses or purposes. When used as absorbent articles, for example, the composite sheets are formed to improve the appearances and skin contact of the absorbent articles, and to expand and contract with the movements of the body or the like.

Furthermore, when used as absorbent articles, nonwoven fabrics having stretch properties are required to have strengths of which the absorbent articles endure use. Conversely, in order to produce absorbent articles with the practicality of use thereof maintained and at low costs, it is required that nonwoven fabrics having low basis weights and nonwoven fabrics having low strengths such as composite sheets are used.

Japanese Unexamined Patent Application Publication No. 2006-89907 discloses a method for subjecting a composite sheet to stretch processing two times in order to reduce damage to the composite sheet, in order to develop extensibility while reducing the damage to the sheet. However, in order to prevent fibers from being cut at the time of the stretch processing and prevent the sheet from being broken in this case, fibers having a high degree of elongation at break must be used. Furthermore, it is considered that a gap between the fibers is increased by extending and cutting the fibers in the stretching processing.

Here, when the gap between the fibers is great, adhesives used for bonding nonwoven fabrics to each other flow out. When the basis weight of the composite sheet is increased in order to prevent the adhesives from flowing out, the production cost is increased, and the practicality of use is adversely affected.

SUMMARY OF THE INVENTION

An objective of the present invention is to provide a composite sheet that can inhibit adhesives from flowing out without increasing the basis weight thereof.

The inventors of the present invention have discovered that a composite sheet smooth to the touch, which has a low basis weight and can prevent hot melt adhesives from flowing out, can be obtained by bonding a stretchable nonwoven fabric formed by mixing elastomer fibers and thermoplastic fibers that can be stretched to a non-stretchable nonwoven fabric with the adhesives with the stretchable nonwoven fabric extended, thereby completing the present invention.

In a first aspect of the present invention, a composite sheet includes a non-stretchable sheet, a stretchable nonwoven fabric having thermoplastic fibers that have been stretched at least partially and elastomer fibers separate from the thermoplastic fibers, and having a plurality of strip-shaped non-dense regions and a plurality of strip-shaped dense regions, which are formed along a first direction, on both of its surfaces such that the strip-shaped non-dense regions are continuously alternated with the strip-shaped dense regions in a second direction perpendicular to the first direction and the strip-shaped dense regions on one of the surfaces are alternated with the strip-shaped dense regions on the other surface in the second direction, and an adhesive portion for laminating the non-stretchable sheet and the stretchable nonwoven fabric.

In a second aspect of the composite sheet as described in the first aspect of the present invention, the thermoplastic fibers include thermoplastic fibers that have not been partially stretched, and thermoplastic fibers that have been partially stretched and have a smaller average fiber diameter than that of the thermoplastic fibers that have not been partially stretched, a region including the thermoplastic fibers that have been partially stretched is the strip-shaped non-dense region, and a region including the thermoplastic fibers that have not been partially stretched is the strip-shaped dense region.

In a third aspect of the composite sheet as described in the first or second aspect of the present invention, the stretchable nonwoven fabric in an extended state is laminated on the non-stretchable sheet.

In a fourth aspect of the composite sheet as described in any one of the first to third aspects of the present invention, the average peel strength thereof in a case where a weight weighing 40 g/cm$^2$ is placed on the two composite sheets overlapped such that the respective surfaces of the stretchable nonwoven fabrics face each other and is left for one week at a room temperature of 50 degrees C. and a humidity of 60% is not more than 0.15 N/50 mm.

In a fifth aspect of the present invention, an absorbent article includes at least an absorbent body and the composite sheet according to any one of the first to fourth aspects of the present invention.

According to the present invention, a composite sheet smooth to the touch, which has a low basis weight and can inhibit adhesives from flowing out can be provided by mixing thermoplastic fibers that can be stretched and elastomer fibers separate from the thermoplastic fibers that can be stretched to form a stretchable nonwoven fabric, and bonding the stretchable nonwoven fabric to a non-stretchable nonwoven fabric with the adhesives with the stretchable nonwoven fabric extended.

DETAILED DESCRIPTION OF THE INVENTION

Embodiments of the present invention are described below. The present invention relates to a composite sheet obtained by subjecting a nonwoven fabric formed by mixing thermoplastic fibers that can be stretched and elastomer fibers separate from the thermoplastic fibers that can be stretched to stretch processing to form a stretchable nonwoven fabric, and bonding the stretchable nonwoven fabric to a non-stretchable nonwoven fabric with adhesives with the stretchable nonwoven fabric extended. The composite sheet according to the present invention, a method for manufacturing the composite sheet, and an absorbent article using the composite sheet are described in detail below.

<Composite Sheet>

Figure 1:
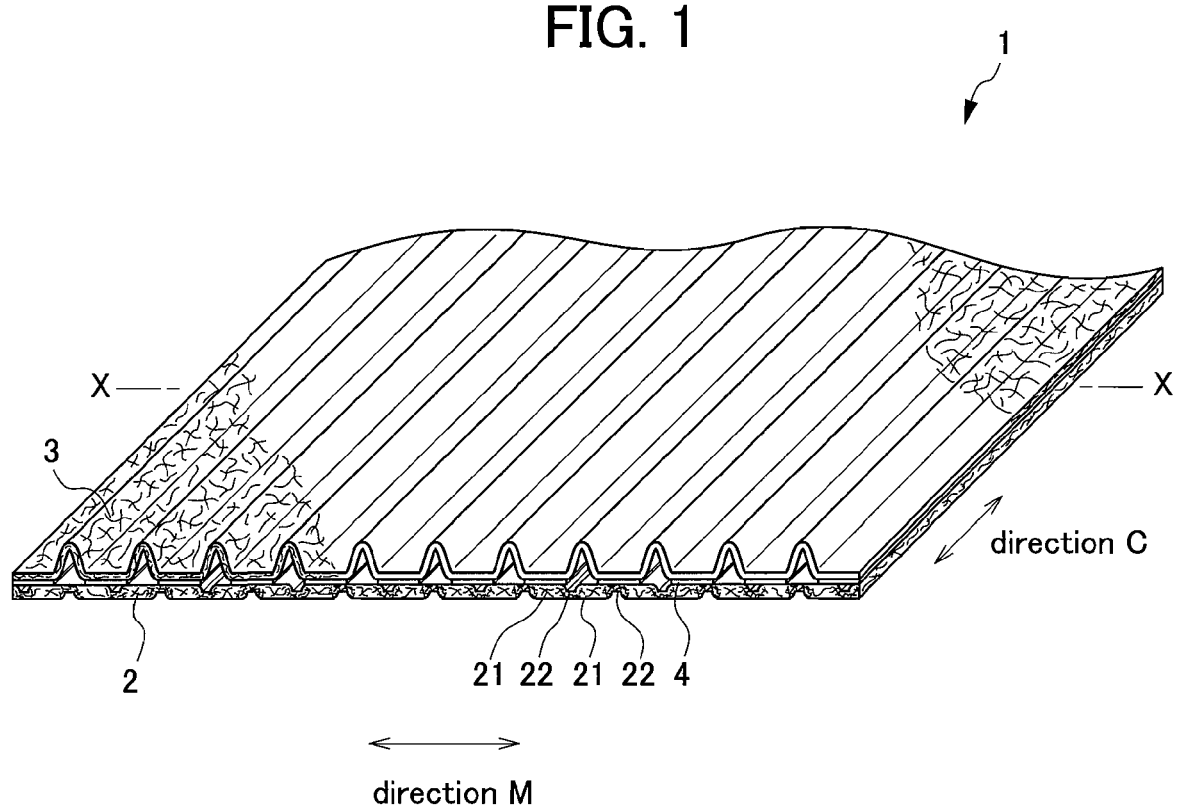
FIG. 1 is a perspective view of a composite sheet according to the present invention.
Figure 2:
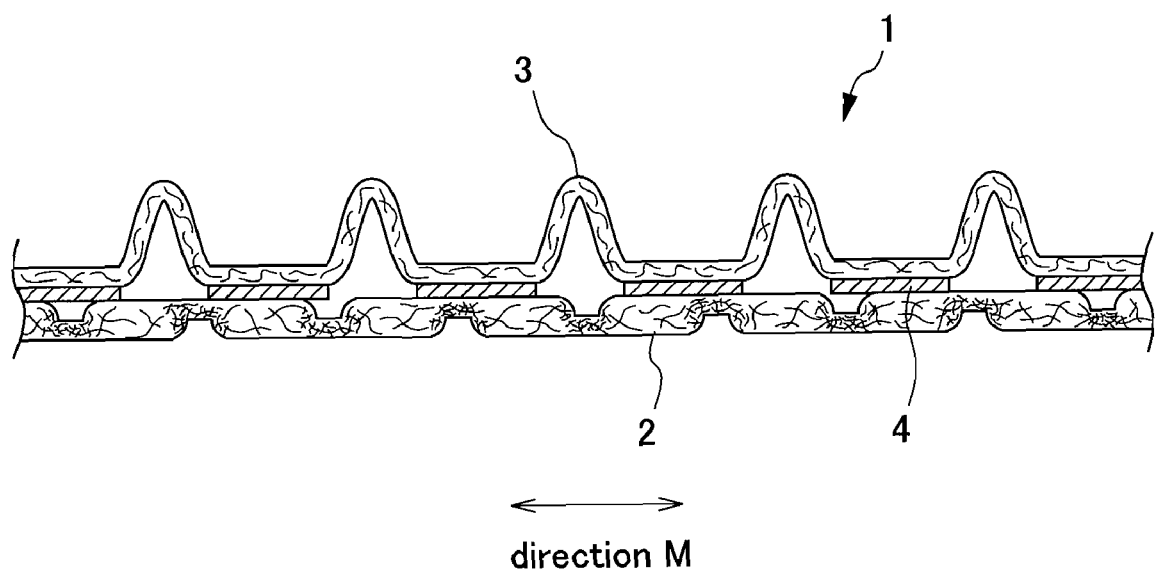
FIG. 2 is a sectional enlarged view in a direction X-X in FIG. 1.

A composite sheet 1 is described with reference to FIGS. 1 to 9. As shown in FIGS. 1 and 2, the composite sheet 1 according to the present invention has a stretchable nonwoven fabric 2 and a non-stretchable nonwoven fabric 3 serving as a non-stretchable sheet bonded to each other with adhesives 4. Specifically, in the composite sheet 1, the stretchable nonwoven fabric 2 is laminated on the non-stretchable nonwoven fabric 3 with the stretchable nonwoven fabric 2 extended.

Figure 6A:
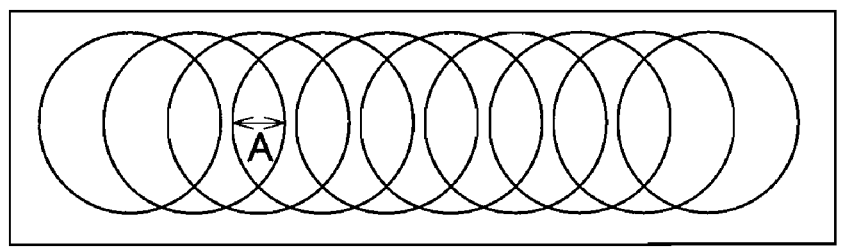
FIG. 6A is a diagram showing an example of a coating pattern of adhesives according to the present invention.
Figure 6B:
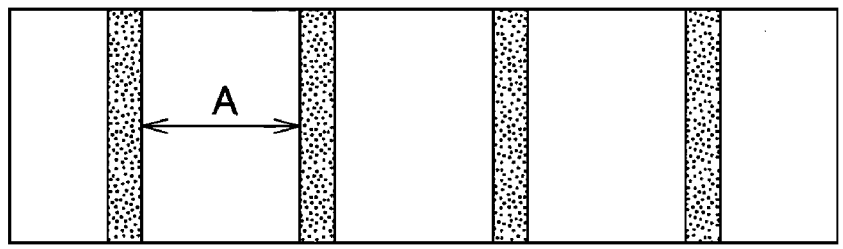
FIG. 6B is a diagram showing an example of a coating pattern of adhesives according to the present invention.

The composite sheet 1 is formed by applying the adhesives 4 to the non-stretchable nonwoven fabric 3 in a strip shape with predetermined spacing to laminate the non-stretchable nonwoven fabric 3 on the stretchable nonwoven fabric 2 in an extended state. Therefore, when the extended state of the stretchable nonwoven fabric 2 is released, the non-stretchable nonwoven fabric 3 is bonded to the stretchable nonwoven fabric 2 in accordance with a coating pattern of the adhesives 4 and has a plurality of wrinkles formed therein in such a form that its unbonded portion sags. The form of the wrinkles is not limited to the form shown in FIG. 2. The form is changed depending on the coating pattern of the adhesives 4, described later. FIG. 2 shows a case where the adhesives 4 are applied with an equal width and with equal spacing, as shown in FIG. 6B. The wrinkles formed in the non-stretchable nonwoven fabric 3 are also substantially equally spaced. Furthermore, the adhesives 4 may be applied to not only the non-stretchable nonwoven fabric 3, but also to the stretchable nonwoven fabric 2.

It is preferable that the basis weight of the composite sheet 1 is not more than 200 g/m², and more specifically 65 to 105 g/m² in a relaxed state. It is preferable that the basis weight of the composite sheet 1 with the composite sheet 1 extended to its natural length in the non-stretchable nonwoven fabric 3 is not more than 130 g/m², and more specifically 30 to 65 g/m².

Here, a first direction (direction C) of the composite sheet 1 and a second direction (direction M) perpendicular to the first direction may be respectively referred to as a longitudinal direction and a transverse direction.

The basis weight of the composite sheet 1 that has been extended to its natural length="laminate basis weight" can be found by the following equation:

laminate basis weight=Basis weight of stretchable nonwoven fabric÷width reduction ratio of stretchable nonwoven fabric÷expansion and contraction magnification+basis weight of non-stretchable nonwoven fabric The width reduction ratio of the stretchable nonwoven fabric indicates the ratio of the length in the first direction (direction C) at the time of extension of the stretchable nonwoven fabric 2 to the length in the first direction (direction C) at the time of relaxation (an unextended state) of the stretchable nonwoven fabric 2. When the stretchable nonwoven fabric 2 is extended, a so-called neck-in phenomenon occurs, so that the length thereof in the first direction (direction C) is reduced.

Figure 3:
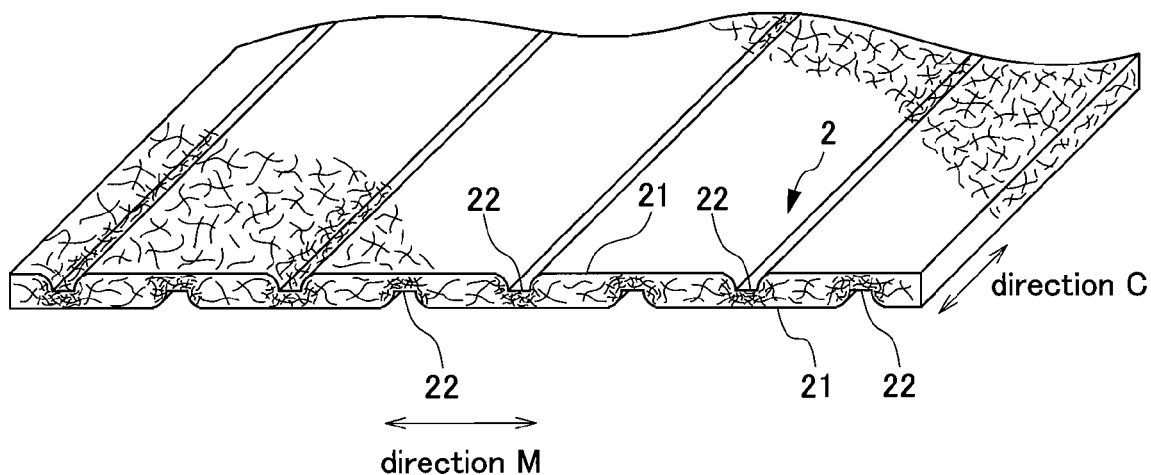
FIG. 3 is a perspective view of a stretchable nonwoven fabric according to the present invention.
Figure 4:
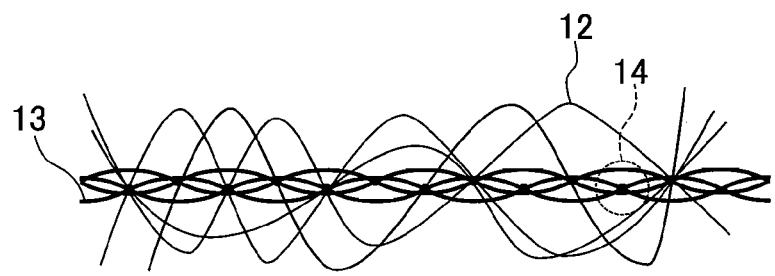
FIG. 4 is a cross-sectional view using a fiber state of the stretchable nonwoven fabric according to the present invention.

As shown in FIG. 3, the stretchable nonwoven fabric 2 has a plurality of strip-shaped non-dense regions 21 and a plurality of strip-shaped dense regions 22 alternately formed on both surfaces thereof. The plurality of dense regions 22 on one of the surfaces are alternated with the plurality of dense regions 22 on the other surface in the width direction of the composite sheet 1. Furthermore, the stretchable nonwoven fabric 2 is formed of thermoplastic fibers 12 that can be stretched and elastomer fibers 13.

The non-dense region 21 includes more thermoplastic fibers 12, which have been stretched by gear-stretch processing and can be stretched as described later, than the dense region 12. Furthermore, the dense region 22 includes more thermoplastic fibers 12, which have not been stretched by gear-stretch processing and can be stretched as described later, than the non-dense region. That is, in the stretchable nonwoven fabric including the dense region 22 formed by gear-stretch processing and the non dense region 21, the mass per unit volume of the dense region 22 is higher than the mass per unit volume of the non-dense region 21.

Although in the non-dense region 21, the elastomer fibers 13 contract to return to the original fiber length even after gear-stretch processing, the thermoplastic fibers 12 that can be stretched, which have been stretched by gear-stretch processing, are kept extended at least partially without returning to the original fiber length. The thermoplastic fibers 12 become expanded in the thickness direction around a compression point 14 by a length corresponding to its extended portion. That is, a gap in the stretchable nonwoven fabric 2 is greater than that before gear-stretch processing. Furthermore, the length of the extended portion of the thermoplastic fibers 12 that can be stretched at least partially by gear-stretch processing is an extension margin of the stretchable nonwoven fabric 2 (composite sheet 1).

In order to inhibit the adhesives 4 from flowing out, it is preferable that the respective average fiber diameters of the thermosetting fibers 12 that can be stretched and the elastomer fibers 13, which constitute the stretchable nonwoven fabric 2, are made to be as small as possible. This inhibits adhesives 4 from flowing out, as described later, because the average distance between the fibers is decreased in the same basis weight. Specifically, it is preferable that the respective average fiber diameters of the thermoplastic fibers 12 that can be stretched and the elastomer fibers 13, which are used for the stretchable nonwoven fabric 2, are 21 to 22 μm.

It can be expected that the average fiber diameter of the thermoplastic fibers 12 that can be stretched in the non-dense region 21 is smaller than the average fiber diameter of the thermoplastic fibers 12 that can be stretched in the dense region 22 by being extended in gear-stretch processing.

Examples of the thermoplastic fibers 12 that can be stretched, which are used for the stretchable nonwoven fabric 2, include polyolefin-based and polyester-based fibers. Specific examples include polypropylene, polyethylene, polyethylene terephthalate, and polybutylene terephthalate.

Furthermore, examples of the elastomer fibers 13 used for the stretchable nonwoven fabric 2 are urethane-based, polystyrene-based, and rubber-based fibers.

An example of the mixture ratio (weight ratio) of the elastomer fibers 13 to the thermoplastic fibers 12 that can be stretched is 80:20 to 25:75. The stretchable nonwoven fabric 2 may be distorted more greatly when the mixture ratio of the thermoplastic fibers 12 that can be stretched is more than 75%, while feeling sticky to the touch when the mixture ratio of the elastomer fibers 13 is more than 80%.

The stretchable nonwoven fabric 2 includes thermoplastic fibers 12 that can be stretched and elastomer fibers 13, and is formed by subjecting a raw stretchable nonwoven fabric 5 having no stretchability to gear-stretch processing. The raw stretchable nonwoven fabric 5 is formed of the abovementioned fiber structure. It is preferable that the basis weight in an unextended state of the stretchable nonwoven fabric 2 is 20 to 100 g/m². When the basis weight of the stretchable nonwoven fabric 2 is less than 20 g/m², the adhesives 4 may flow out. On the other hand, when the basis weight of the stretchable nonwoven fabric 2 is more than 100 g/m², the stretchable-nonwoven fabric 2 is not suitable for an absorbent article in terms of distortion and tensile strength when used for the absorbent article.

Gear-stretch processing indicates processing for compressing the raw stretchable nonwoven fabric 5 by a pair of shaping rolls 10 and 10' serving as so-called mesh embossing rolls, extending the thermoplastic fibers 12 that can be stretched, and causing the raw stretchable nonwoven fabric 5 to have stretchability based on the stretchability of the elastomer fibers 13. Gear-stretch processing is described with reference to FIG. 5.

Each of the paired shaping rolls 10 and 10' used for gear-stretch processing includes a toothed region 11 having a plurality of grooves or a plurality of gear teeth 111. The shaping rolls 10 and 10' rotate opposite to each other with their toothed regions 11 meshed with each other in order to compress the raw stretchable nonwoven fabric 5. The dense region 22 is formed in a portion that is compressed by a apex portion of the meshed gear tooth 111 in the raw stretchable nonwoven fabric 5. Furthermore, a portion that is not compressed by the gear tooth 111 in the raw stretchable nonwoven fabric 5 (a portion in contact with a side surface of the gear tooth 111) is extended by the meshed gear tooth 111 so that the fibers extend. Therefore, the non-dense region 21 is formed in the portion.

The plurality of non-dense regions 21 and the plurality of dense regions 22 are thus alternately formed in a strip shape for each gap between the teeth 111 in the toothed region 11. That is, the non-dense regions 21 and the dense regions 22 are alternately formed parallel to the longitudinal direction (direction C) serving as the first direction in the stretchable nonwoven fabric 2.

As described above, the plurality of non-dense regions 21 and the plurality of dense regions 22 are alternately formed with substantially equal spacing in accordance with the shape at the tip of each of the gear teeth 111 and the depth of the groove formed by the two adjacent gear teeth 111. In other words, the length in the longitudinal direction (direction C) of the non-dense region 21 and the dense region 22 is determined in accordance with the size of the gear teeth 111 in the pair of shaping rolls 10 and 10'.

Usable as the shape at the tip of the gear tooth 111 can be an acute-angled shape, a shape having a substantially flat surface at its top, or a shape that is substantially circular in a cross section parallel to a concentric shape of the shaping rolls 10 and 10'.

Furthermore, the expansion and contraction direction of the stretchable nonwoven fabric 2 can be optionally formed in accordance with the intended use of the stretchable nonwoven fabric 2 or the composite sheet 1. That is, the stretchable nonwoven fabric 2 can be extended in one of the transverse direction (direction M) and the longitudinal direction (direction C) depending on the direction in which the toothed regions 11 are arranged when gear-stretch processing is performed. For example, when the toothed region 11 is arranged so as to be perpendicular to the transverse direction (direction M) of the raw stretchable nonwoven fabric 5 before gear-stretch processing, the stretchable nonwoven fabric 2 extends in the transverse direction (direction M). When the toothed region 11 is arranged so as to be parallel to the transverse direction (direction M) of the raw stretchable nonwoven fabric 5 before gear-stretch processing, the stretchable nonwoven fabric 2 extends in the longitudinal direction (direction C). Furthermore, gear-stretch processing is performed twice in the transverse direction (direction M) and the longitudinal direction (direction C) so that the stretchable nonwoven fabric 2 can be formed that can be stretched in both the directions.

Examples of the non-stretchable nonwoven fabric 3 to be laminated on the abovementioned stretchable nonwoven fabric 2 include various types of known nonwoven fabrics such as a spunbonded nonwoven fabric, a meltblown nonwoven fabric, an SMS nonwoven fabric that is a combination of a spunbonded nonwoven fabric and a meltblown nonwoven fabric, an air-through nonwoven fabric, a spun-lace nonwoven fabric, and an airlaid nonwoven fabric, which can be changed, as needed, in accordance with the intended use. Furthermore, the non-stretchable nonwoven fabric 3 to be bonded is not limited to a single layer. It may be multi-layer. Alternatively, it may be partially multi-layer in accordance with the intended use.

It is preferable that the basis weight of the non-stretchable nonwoven fabric 3 is 10 to 50 g/m² in an extended state. When the basis weight of the non-stretchable nonwoven fabric 3 is less than 10 g/m², the maximum strength of the composite sheet 1 may be insufficient. When the basis weight of the non-stretchable nonwoven fabric 3 is more than 50 g/m², the return strength of the non-stretchable nonwoven fabric 3 is insufficient for the rigidity thereof. Therefore, the degree of elongation of the composite sheet 1 cannot, in some cases, be ensured.

The composite sheet 1 is formed by bonding the stretchable nonwoven fabric 2 and the non-stretchable nonwoven fabric 3 to each other with the adhesive 4. The adhesive 4 to be used is preferably a hot-melt adhesive. The composite sheet 1 is formed by bonding the stretchable nonwoven fabric 2 to the non-stretchable nonwoven fabric 3 with the adhesive 4 with the stretchable nonwoven fabric 2 extended.

At this time, it is preferable that the stretchable nonwoven fabric 2 is bonded to the non-stretchable nonwoven fabric 3 with the stretchable nonwoven fabric 2 extended such that the length thereof is increased by a predetermined factor. Thus, with the extension released after the stretchable nonwoven fabric 2 and the non-stretchable nonwoven fabric 3 are bonded to each other, wrinkles are formed in the non-stretchable nonwoven fabric 3 as the stretchable nonwoven fabric 2 contracts. As shown in FIG. 2, the non-stretchable nonwoven fabric 3 is partially bonded and fixed to the stretchable nonwoven fabric 2 with the adhesive 4, so that the whole composite sheet 1 expands and contracts with the wrinkles formed in the non-stretchable nonwoven fabric 3 used as an extension margin.

The adhesive 4 may be applied to either the stretchable nonwoven fabric 2 or the non-stretchable nonwoven fabric 3. Furthermore, as a method/pattern for applying the hot-melt adhesive, any method/pattern can be selected from pattern processing such as curtain spray, spiral, omega, dot shape, full coating, dot aggregate, slot coating, and roll coater.

When a pattern other than curtain spray or the full coating is selected, it is preferable that spacing A between adjacent hot-melt joints (see FIGS. 6A and 6B) is less than 15 mm, and more preferably less than 10 mm. For example, the coating pattern of the adhesive 4 shown in FIG. 6A is the spiral pattern, and the coating pattern shown in FIG. 6B is an intermittent coating pattern by the roll coater. when the spacing A between the joints becomes enlarged, the appearance is degraded because the appearance of wrinkles is increased, and fingers enter a non-joining portion when the nonwoven fabric is used for an absorbent article, described later, thereby causing a break to occur.

Figure 7:
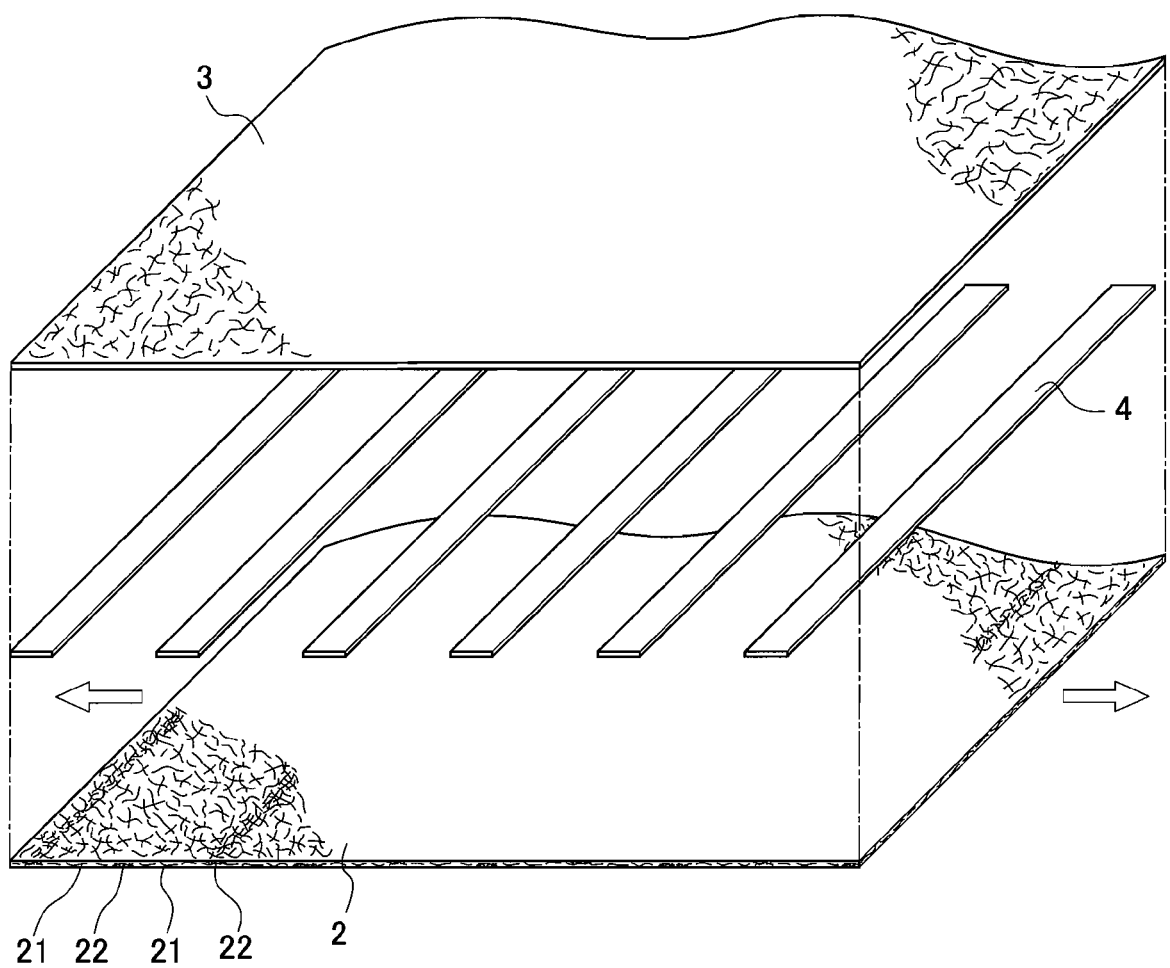
FIG. 7 is a diagram showing an example in which the stretchable nonwoven fabric according to the present invention is coated with adhesives in the coating pattern shown in FIG. 6B.
Figure 8:
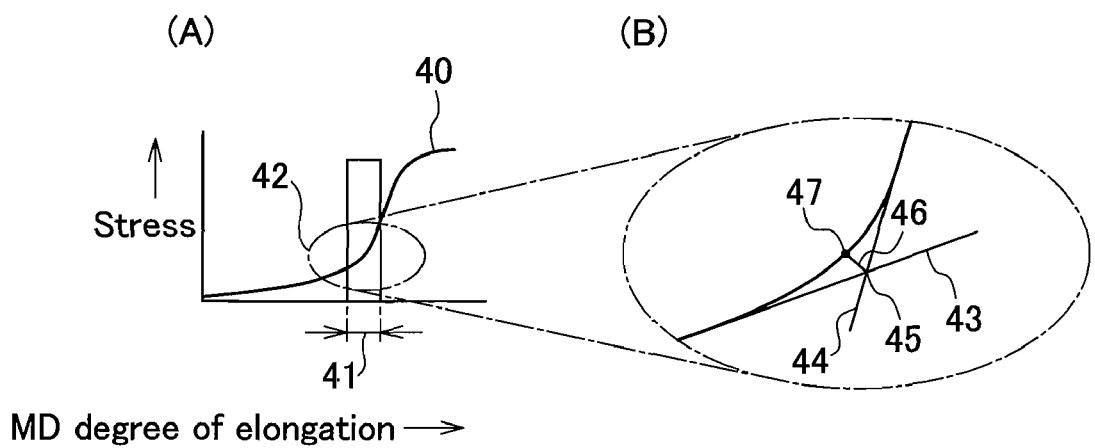
FIG. 8A is a diagram illustrating the tensile strength per predetermined width of the composite sheet according to the present invention at the time of extension thereof.
FIG. 8B is a partially enlarged view of FIG. 8A.

The adhesive 4 is applied to the stretchable nonwoven fabric 2 in a strip shape with equal spacing, and is bonded to the non-stretchable nonwoven fabric 3, as shown in FIG. 7, for example.

It is preferable that the basis weight of the adhesive 4 is 0.5 to 15 g/m$^2$. When the basis weight is less than 0.5 g/m$^2$, the nonwoven fabrics may, in some cases, be peeled. Furthermore, when the basis weight is more than 15 g/m$^2$, the flexibility of the composite sheet is degraded, so that the adhesive 4 may, in some case, flow out.

The flowing of the adhesive 4 in the composite sheet 1 according to the present invention can be measured by the average peel strength. When the average peel strength is great, the adhesive 4 flows out so that the stretchable nonwoven fabric is bonded to others. Consequently, the lower the peel strength is, the less the flowing of the adhesive is.

The average peel strength is measured in the following way. That is, a raw stretchable nonwoven fabric 5 is subjected to gear-stretch processing to form a stretchable nonwoven fabric 2. The formed stretchable nonwoven fabric 2 is extended by 1.8 times, and is laminated on a non-stretchable nonwoven fabric 3 to manufacture a composite sheet 1. Such composite sheets 1 are prepared in sets of two. The two composite sheets 1 are brought into a relaxed state, and are overlapped such that their surfaces on the side of the stretchable nonwoven fabrics 2 face each other after being cut to dimensions of 100 mm in the transverse direction (direction M) and 50 mm in the longitudinal direction (direction C). A weight weighing 40 g/cm$^2$ is placed thereon. An example of the weight weighing 40 g/cm$^2$ is a weight having dimensions of 50 mm by 50 mm and weighing 1 kg. Thereafter, the average peel strength (unit of N/50 mm) of a sample left for one week at an ambient temperature of 50 degrees C. and a humidity of 60% is measured by a width of 50 mm, a distance between chucks set to 30 mm and at a peel rate of 100 mm/min using a tensile tester (Autograph Tensile Tester (AG-1kNI) manufactured by SHIMADZU CORPORATION).

It is preferable that the average peel strength is 0 to 0.15 N/50 mm. When the average peel strength exceeds 0.15 N/50 mm, an absorbent article using the composite sheet 1 may feel sticky when used. Furthermore, adjacent pieces may stick together within a package of the absorbent article and a folded product may be difficult to spread.

It is preferable that the ratio of expansion and contraction of the composite sheet 1 is not less than 20%. Furthermore, it is preferable that as the ratio of expansion and contraction of the stretchable nonwoven fabric 2, the degree of fully-stretched elongation is not less than 20%.

Here, the degree of fully-stretched elongation indicates that when two tangents 43 and 44 to a curve 40 in a tensile test shown in FIG. 8A are drawn (FIG. 8B), a line 46 for dividing an angle formed by the two tangents into two equal parts is drawn with their intersection 45 as a starting point, and the intersection of the line 46 and the curve 40 is taken as a point 47, the degree of fully-stretched elongation is at the point 47.

A method for measuring the ratio of expansion and contraction of the composite sheet 1 is described. First, let Y be the length of the composite sheet 1 with the composite sheet 1 extended to the fully-stretched length in the expansion and contraction direction thereof (the original length thereof with the non-stretchable nonwoven fabric 3 laminated on the stretchable nonwoven fabric 2), and y be the contraction length of the composite sheet 1 that naturally contracts because it is left in a natural state with the extension released. Y and y are substituted in the following equation:

The ratio of expansion and contraction(%)= Y/y×100−100

The ratio of expansion and contraction may be found using the foregoing equation by putting marks with predetermined spacing (e.g., 100 mm) in the expansion and contraction direction with the composite sheet 1 contracting, and measuring the length between the marks with the composite sheet 1 extended to the fully-stretched length in the expansion and contraction direction.

The respective directions of the stretchable nonwoven fabric 2 and the non-stretchable nonwoven fabric 3 at the time of bonding can be optionally selected in accordance with the intended use or the like of the composite sheet 1. For example, when the stretchable nonwoven fabric 2 has stretch properties in the transverse direction (direction M), the stretchable nonwoven fabric 3 can be selected to be either the transverse direction (direction M) or the longitudinal direction (direction C). When the stretchable nonwoven fabric 2 has stretch properties in the longitudinal direction (direction C), the stretchable nonwoven fabric 3 can also be selected to be either the transverse direction (direction M) or the longitudinal direction (direction C). Furthermore, even when the composite sheet 1 is composed of three or more layers, the nonwoven fabric to be bonded can be selected to be both the transverse direction (direction M) and the longitudinal direction (direction C).

A combination of the directions of bonding between the stretchable nonwoven fabric 2 and the non-stretchable nonwoven fabric 3 can be optionally selected in accordance with the intended use or the like. Therefore, by considering the most suitable balance corresponding to the intended use, the composite sheet 1 can be manufactured for the tensile strength. The reason for this is that the nonwoven fabric generally varies in the maximum strength depending on whether it is selected to be the longitudinal direction (direction C) or the transverse direction (direction M). Furthermore, the stretchable nonwoven fabric 2 also differs in the tensile strength even in the same basis weight depending on the direction in which gear-stretch processing is performed.

<Method of Manufacturing Composite Sheet>

Figure 9:
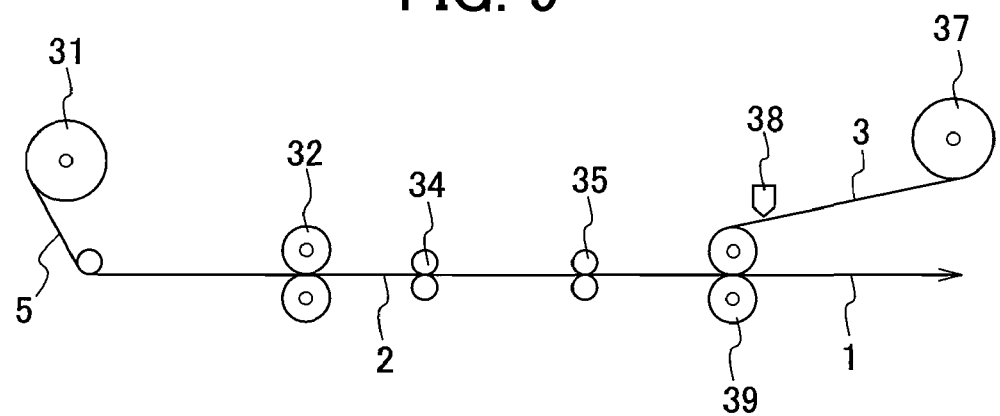
FIG. 9 is a diagram for explaining a method of manufacturing the composite sheet according to the present invention.

A method of manufacturing a composite sheet 1 is described with reference to FIG. 9. The method of manufacturing the composite sheet 1 according to the present invention is carried out in the following way. First, a raw stretchable nonwoven fabric 5 before gear-stretch processing, which is wound around a raw fabric roll 31, is wound off.

Gear-stretch processing is then performed. The raw stretchable nonwoven fabric 5 is inserted between a pair of gear rolls 32 formed such that their respective toothed regions 11 are meshed with each other, as described above (FIG. 5). A thermoplastic fiber 12 that can be stretched, which is sandwiched between the teethed regions 11, is extended. As the expansion and contraction direction, either the transverse direction (direction M) or the longitudinal direction (direction C) can be selected in accordance with the intended use of the composite sheet 1. The raw stretchable nonwoven fabric 5 can be subjected to gear-stretch processing twice in different directions in a case where the composite sheet 1 is made stretchable in both of the directions. That is, after stretch properties are developed in one of the transverse direction (direction M) and the longitudinal direction (direction C), gear-stretch processing is performed in the other direction for the second time. In order to make the composite sheet 1 stretchable in both of the directions, gear-stretch processing need not necessarily be performed twice. The composite sheet 1 can be made stretchable in both of the directions by performing gear-stretching process in the transverse direction (direction M) in the present embodiment.

A stretchable nonwoven fabric 2 having stretchability developed is extended by rolls 34 and 35, and is further passed between nip rolls 39. On the other hand, a non-stretchable nonwoven fabric 3 wound around a raw fabric roll 37 is coated with hot-melt adhesive using an adhesive coater 38, and is passed between the paired nip rolls 39. The stretchable nonwoven fabric 2 and the non-stretchable nonwoven fabric 3 can be laminated by simultaneously passing the stretchable nonwoven fabric 2 and the non-stretchable nonwoven fabric 3 between the nip rolls 39. Thereafter, the composite sheet 1 can be obtained by releasing an extended state.

<Absorbent Article>

The composite sheet 1 according to the present invention can be employed for a pants-type disposable diaper 50 serving as an absorbent article, for example. Although a pants-type disposable diaper 50 using the abovementioned composite sheet 1 is described in detail below, a surface, directed toward the body of a wearer, of the pants-type disposable diaper 50 is considered a skin contacting side, and a surface on the opposite side of the skin contacting side is considered a non-skin contacting side.

Figure 10:
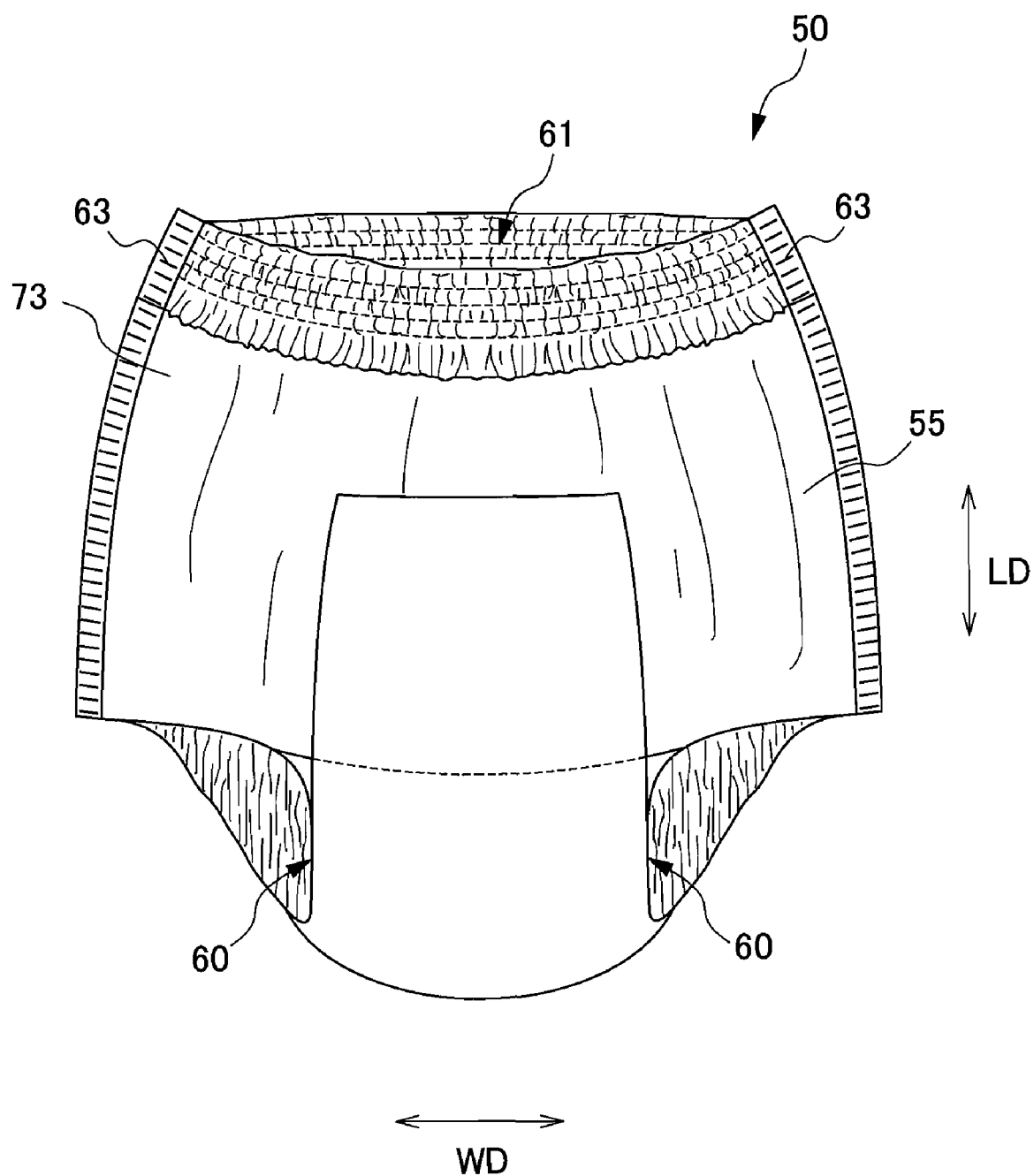
FIG. 10 is a front view showing a disposable diaper serving as an example of an absorbent article using the composite sheet according to the present invention.
Figure 11:
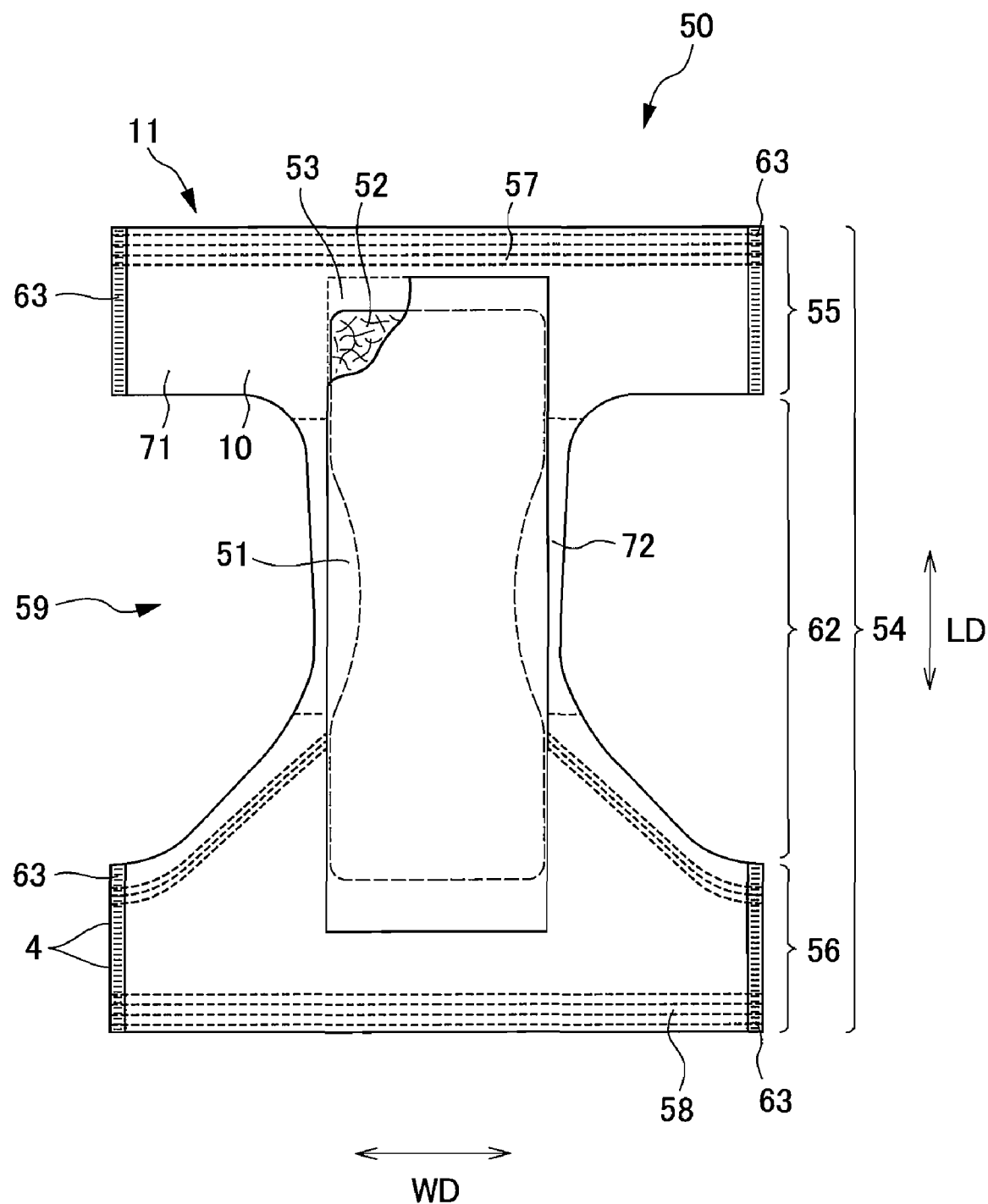
FIG. 11 is a development elevation of the disposable diaper according to the present invention.

As shown in FIGS. 10 and 11, a pants-type disposable diaper body includes a chassis 54 forming the main body of the pants-type disposable diaper 50, a liquid-permeable front surface sheet 51 arranged on a surface, on the side of the skin contacting side of the chassis 54, a liquid-impermeable back surface sheet 53 arranged on a surface on the side of the non-skin contacting side of the chassis 54, and an absorbent core 52 having liquid retaining properties and sandwiched between the front surface sheet 51 and the chassis 54.

Figure 5:
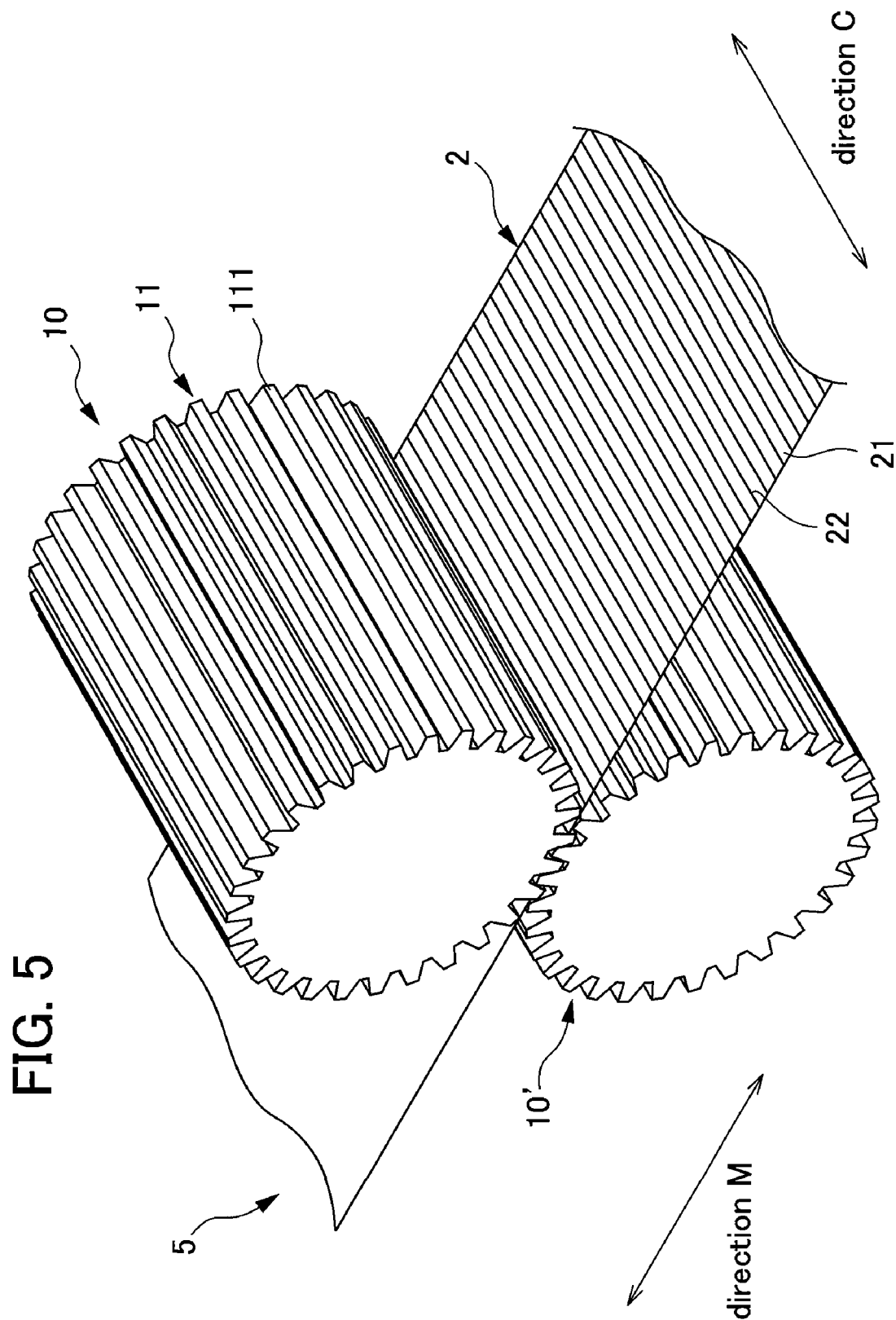
FIG. 5 is a diagram illustrating a state where a raw stretchable nonwoven fabric according to the present invention is subjected to stretch processing using a mesh embossing roll.

The chassis 54 is formed in the shape of pants by a front body portion 55 and a rear body portion 56, and includes a front waist gather 57 forming an end of the front body portion 55 and a rear waist gather 58 forming an end of the rear body portion 56. The gathers are formed by arranging an elastic member such as a rubber thread around the trunk of the wearer so as to be substantially parallel thereto along a width direction (WD) at respective ends of the front body portion 55 and the rear body portion 56. Here, the width direction (WD) refers to a direction around the trunk of the wearer with the pants-type disposable diaper 50 worn on the body of the wearer. A direction perpendicular to the width direction (WD) is taken as a longitudinal direction (LD). Therefore, when the stretchable nonwoven fabric 2 that has been subjected to gear-stretch processing in the transverse direction (direction M), as shown in FIG. 5, is used, the front body portion 55 has stretchability in the width direction (WD) when the direction in which the stretchable nonwoven fabric 2 stretches (the direction M) is along the width direction (WD) of the front body portion 55, for example. Notches 59 having a substantially U-shape are respectively formed toward the inside of the chassis 54 on both sides in the longitudinal direction (LD) of the chassis 54. The notches 59 respectively form leg openings 60 when the front body portion 55 and the rear body portion 56 of the chassis 54 are joined to each other by joining portions 63 to have the shape of pants, as shown in FIG. 10. Furthermore, the front body portion 55 and the rear body portion 56 are joined to each other to form a waist opening 61.

As shown in FIG. 11, the chassis 54 includes a crotch region 62. The crotch region 62 is sandwiched between the notches 59 on both sides thereof. The absorbent core 52 having liquid retaining properties formed in a substantially vertically-long shape composing an absorbing layer is arranged on a surface on the side of the skin contacting side of the crotch region 62. Furthermore, the liquid-permeable front surface sheet 51 and the liquid-impermeable back surface sheet 53 are arranged on a surface on the side of the skin contacting side of the absorbent core 52 and on a surface on the side of the non-skin contacting side of the crotch region 62, respectively.

Here, the chassis 54 includes a base sheet 71 serving as a non-stretchable nonwoven fabric, a pair of crotch-side sheets 72 serving as a first stretchable nonwoven fabric formed of the stretchable nonwoven fabric 2 arranged so as to have stretchability in the longitudinal direction (LD) of the absorbent core 52, and a sheathing sheet 73 serving as a second stretchable nonwoven fabric formed of the stretchable nonwoven fabric 2 arranged so as to have stretchability in the width direction (WD).

The non-stretchable base sheet 71 is a spunbonded nonwoven fabric weighing 19 g/m$^2$, for example, and serves as a main body portion constituting the chassis 54. That is, the crotch-side sheets 72 and the sheathing sheet 73, described later, are joined to a surface on the side of the non-skin contacting side of the base sheet 71 to constitute the chassis 54.

The crotch-side sheets 72 are respectively arranged in both side parts of the crotch region 62 in the chassis 54 and on the surface on the side of the non-skin contacting side, of the base sheet 71. The crotch-side sheet 72 is a nonwoven fabric having stretch properties in the longitudinal direction (LD) and having no stretch properties in the width direction (WD). That is, the crotch-side sheet is formed by arranging, after bringing the stretchable nonwoven fabric 2 (it can be formed that the gear tooth 111 in FIG. 5 is placed to MD direction so that direction of expansion and contract of the stretchable nonwoven fabric 2 is CD direction.) that has been subjected to gear-stretch processing in the longitudinal direction (direction C), for example, in an extended state from an unextended state so as to have a length that is 1.9 times that in the unextended state so that direction of expansion and contract of the stretchable nonwoven fabric 2 is the longitudinal direction (LD), and bonding the stretchable nonwoven fabric 2 to the base sheet 71 (the non-stretchable nonwoven fabric 3) with hot-melt adhesive. That is, the crotch-side sheet 72 is a composite sheet 1 joined to the base sheet 71.

The sheathing sheet 73 is a stretchable nonwoven fabric 2 arranged so as to cover the surface on the side of the non-skin contacting side of the base sheet 71 in the chassis 54 and the whole surface other than the front waist gather 57 and the rear waist gather 58. The sheathing sheet 73 has stretch properties in the width direction (WD) and has no stretch properties in the longitudinal direction (LD). That is, the sheathing sheet 73 is formed by arranging, after bringing the stretchable nonwoven fabric 2 (FIG. 5) that has been subjected to gear-stretch processing in the transverse direction (direction M), for example, into an extended state from an unextended state so as to have a length that is 1.8 times that in the unextended state so that the direction of expansion and contraction of the stretchable nonwoven fabric 2 is the width direction (WD), and bonding the stretchable nonwoven fabric 2 to the base sheet 71 (the non-stretchable nonwoven fabric 3) with hot-melt adhesive. That is, the sheathing sheet 73 is a composite sheet 1 joined to the base sheet 71.

Thus, the chassis 54 is a composite sheet 1, which is partially triple layered, obtained by arranging crotch-side sheets 72 on a surface on the side of non-skin contacting side of the base sheet 71 and on both sides of the crotch region 62, further arranging the sheathing sheet 73 on the surface on the side of the non-skin contacting side, and respectively joining both the crotch-side sheets 72 and the sheathing sheet 73 to the base sheet 71 with hot-melt adhesive.

When the front body portion 55 and the rear body portion 56 in the chassis 54 are joined to each other to have the shape of pants, the leg openings (FIG. 10) has stretch properties along the notches 59 by the crotch-side sheets 72. Furthermore, the front body portion 55 and the rear body portion 56 have stretch properties along the outer periphery of the shape of pants by the sheathing sheet 73. Therefore, in the pants-type disposable diaper 50, the chassis 54 itself has stretch properties with the movement of the body.

<Method of Manufacturing Absorbent Article>

Figure 12:
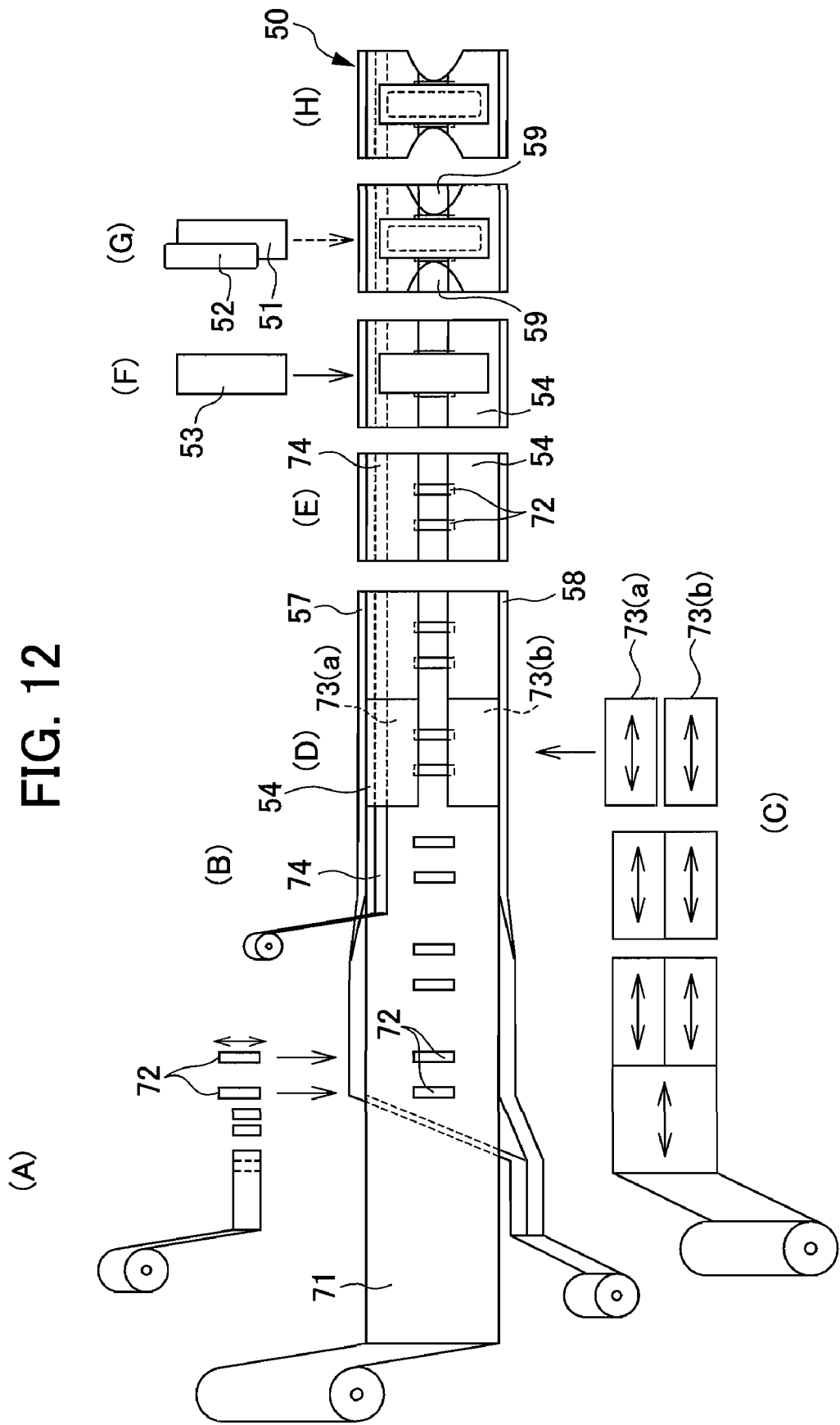
FIG. 12 is a diagram illustrating processes of manufacturing the disposable diaper according to the present invention.

A method of manufacturing a pants-type disposable diaper 50 serving as an absorbent article is described below. FIG. 12 is a diagram illustrating processes of manufacturing the disposable diaper 50, where a surface on the side of the non-skin contacting side of the disposable diaper 50 is considered a front surface, and a surface thereof on the side of the skin contacting side is considered a back surface.

First, a stretchable nonwoven fabric 2 serving as a crotch-side sheet 72 is bonded to a predetermined position with hot-melt adhesive on a surface on the side of the non-skin contacting side of the disposable diaper 50 of a base sheet 71 serving as a non-stretchable nonwoven fabric (FIG. 12 (A)). The stretchable nonwoven fabric 2 is bonded in a state where it is cut to a predetermined size, and is extended by 1.9 times, for example. The stretchable nonwoven fabric 2 may be similarly bonded with hot melt adhesives with the non-stretchable sheet 74 arranged as reinforcement at an end of a front body portion 55 or a rear body portion 56 at this time. Furthermore, sheets for forming a front waist gather 57 and a rear waist gather 58 are bonded to the front body portion 55 and the rear body portion 56 with hot-melt adhesive, respectively (FIG. 12(B)).

On the other hand, as shown in FIG. 12(C), the stretchable nonwoven fabric 2 is cut in a width direction (WD) in a state where it is extended by 1.8 times, for example, and a first sheathing sheet 73 (*a*) arranged on the front body side and a second sheathing sheet 73 (*b*) arranged on the rear body side are further formed. The first sheathing sheet 73 (*a*) and the second sheathing sheet 73 (*b*) are arranged on the surface on the side of the non-skin contacting side, that is on the side on which the crotch-side sheet 72 is arranged of the base sheet 71 with the shielding sheets respectively extended, and are bonded thereto with hot-melt adhesive (FIGS. 12(D) and 12(E)).

A back surface sheet 53 is arranged on a surface on the side of the non-skin contacting side (a surface, on the same side as the side on which the crotch-side sheet 72 and the sheathing sheet 73 are arranged) of a chassis 54 thus formed (FIG. 12(F)). A front surface sheet 51 and an absorbent core 52 are arranged on a surface on the side of the skin contacting side (a surface on the side opposite to the side on which the back surface sheet 53 is arranged) of the chassis 54, and are bonded thereto with hot-melt adhesive or the like (FIG. 12(G)). In order to form leg openings 60, U-shaped notches 59 are respectively cut out with a cutter so as to be recessed toward the inside of the chassis 54 in side parts of the chassis 54 (FIG. 12(H)). Furthermore, the front body portion 55 or the rear body portion 56 is folded toward the skin contacting side so that both side parts of the front body portion 55 and both side parts of the rear body portion 56 are respectively joined to each other to form the shape of pants, thereby forming the pants-type disposable diaper 50 (not shown). Although the first sheathing sheet 73 (*a*) and the second sheathing sheet 73 (*b*) are bonded to the base sheet 71 after being respectively cut, the first sheathing sheet 73 (*a*) and the second sheathing sheet 73 (*b*) may be respectively bonded to the base sheet 71 in a continuous state to bond the absorbent core 52 or the like thereto after the notches 59 are formed. The front body portion 55 and the rear body portion 56 may be joined to each other by the joining portions 63 with the body portion folded in half toward the skin contacting side and finally separated from each other in the shape of pants.

Although in the present embodiment, a description is provided of a disposable diaper having the waist opening 61 and the pair of leg openings 60 by joining the front body portion 55 and the rear body portion 56 to each other at the predetermined joining portions 63, and formed in the shape of pants, as shown in FIGS. 10 and 11, the present invention is not limited to the same. For example, the present invention may be used for an unfolded-type disposable diaper that can be worn by locking a front body portion 55 and a rear body portion 56 using a locking member or the like. Alternatively, the present invention may be used for a disposable diaper formed in the shape of pants, which is locked by a locking member such as a re-lockable surface fastener, as used for the unfolded-type disposable diaper, at predetermined joining portions 63 of a front body portion 55 and a rear body portion 56, is easily unlocked, and can be folded and relocked.

Furthermore, in the present embodiment, the crotch-side sheets 72 and leakage-prevention walls formed of a leakage-prevention sheet, i.e. leg gathers (not shown), may be respectively arranged along both ends in the width direction (WD) of the absorbent core 52 in the disposable diaper. Specifically, the leakage-prevention sheet may be provided so as to extend in the width direction (WD) of the absorbent core 52 from a region between the absorbent core 52 and the chassis 54 or the back surface sheet 53, and at least one crotch-side sheet 72 may be arranged at an end in the width direction (WD) of the leakage-prevention sheet and fixed thereto with hot-melt adhesive or the like. The leakage-prevention sheet may remain extended in the width direction (WD) of the absorbent core 52. Alternatively, the leakage-prevention sheet may be folded toward the center in the width direction (WD) of the absorbent core 52 so that its folded portion is arranged on a surface on the side of the skin contact surface of the absorbent core 52.

Although the back surface sheet 53 is arranged on an outermost surface of the chassis 54, the present invention is not limited to the same. For example, the back surface sheet 53 may be provided between the absorbent core 52 and the chassis 54. Alternatively, when the chassis 54 is formed of a plurality of sheets, the back surface sheet 53 may be provided between the sheets.

In the present invention, although the crotch-side sheets 72 and the sheathing sheet 73 that have developed stretch properties throughout are bonded to the base sheet 71 in respectively extended states to form the composite sheet 1 that has developed stretch properties, the present invention is not limited to the same. For example, the sheathing sheet 73 that has partially developed stretch properties by being subjected to gear-stretch processing may be bonded to the base sheet 71. Furthermore, the number of times of gear-stretch processing is not limited to one. Gear-stretch processing may be performed twice in different directions, as described above, to form a stretchable nonwoven fabric 2 that has developed stretch properties in the longitudinal direction (direction C) and the transverse direction (direction M). Furthermore, the stretchable nonwoven fabric 2 or the non-stretchable nonwoven fabric 3 to be bonded is not limited to a single layer. It may have a plurality of layers overlapped with and bonded to one another. This allows the strength of the composite sheet 1 to be formed high.

Although in the present embodiment, the composite sheet 1 is described as a pants-type disposable diaper, the composite sheet 1 can be also employed as other products. For example, the composite sheet can be employed as a side stretchable sheet of a side-flap or side-stretchable pants-type diaper in an absorbent article of a taping type, a wing for fixing to underwear in a napkin, a stretchable member such as a cuff of a disposable surgical gown, an ear band of a disposable mask, a disposable bandage, a surface material of fomentations, and so on.

INVENTIVE EXAMPLES

While preferred embodiments of the present invention have been described and illustrated above, it is to be understood that they are exemplary of the invention and are not to be considered to be limiting.

A raw stretchable nonwoven fabric 5 in which the mixture ratio (weight ratio) of polypropylene fibers (PP) to polyurethane fibers (TPU) was 55:45 was manufactured. The raw stretchable nonwoven fabric 5 was then subjected to gear-stretch processing using shaping rolls 10 and 10' in order to obtain a stretchable nonwoven fabric 2. The basis weight of the raw stretchable nonwoven fabric 5 was 35 g/m², and the basis weight in a relaxed state of the stretchable nonwoven fabric 2 was 38 g/m².

The stretchable nonwoven fabric 2 was bonded to a non-stretchable nonwoven fabric 3 by hot-melt adhesive with the stretchable nonwoven fabric 2 extended by 1.88 times. A coating pattern of the hot-melt adhesive was spiral coating, and the basis weight of the hot-melt adhesive was 5 g/m² (this is taken as an example 1).

In addition, an example 2 in which the average fiber diameter of the stretchable nonwoven fabric 2 differed from that in the example 1, and a comparative example in which the average fiber diameter of the stretchable nonwoven fabric 2 was the same as that in the example 2 and heating treatment was not performed before gear-stretch processing, were manufactured, and the respective peel strengths and basis weights were measured, as in example 1.

The results of the test are shown in Table 1.

TABLE 1

| | Example 1 | Example 2 | Comparative example |
|---|---|---|---|
| Average fiber diameter (μm) | 22.5 | 26.5 | 26.2 |
| Peel strength (N/50 mm in width) | 0.04 | 0.13 | 0.17 |
| basis weight of the stretchable nonwoven fabric in composite sheet (g/m²) | 25 | 27.5 | 27.5 |
| Heating before expansion and contraction processing | ○ | ○ | x |

From Table 1, a comparison between example 1 and example 2 shows that although the flowing of adhesive is short of a problem level in both examples 1 and 2, the flowing is less, although the basis weight of the stretchable nonwoven fabric is lower in the example 1. Therefore, the smaller the average fiber diameter is, the less the flowing of adhesive is. Furthermore, comparison of example 1, example 2, and the comparative example show that heating before expansion and contraction processing is also effective for the flowing of adhesive.

What is claimed is:

1. A composite sheet comprising:
a non-stretchable sheet;
a stretchable nonwoven fabric having thermoplastic fibers that have stretched at least partially, thermoplastic fibers that have not stretched at least partially and elastomer fibers separate from the thermoplastic fibers, and having a plurality of strip-shaped non-dense regions and a plurality of strip-shaped dense regions, which are formed along a first direction, formed on both surfaces thereof such that the strip-shaped non-dense regions are continuously alternated with the strip-shaped dense regions in a second direction perpendicular to the first direction, and the strip-shaped dense regions on one of the surfaces are alternated with the strip-shaped dense regions on the other surface in the second direction; and
an adhesive portion for laminating the non-stretchable sheet and the stretchable nonwoven fabric,
wherein each of the strip-shaped non-dense regions is expanded in a thickness direction of the stretchable nonwoven fabric as compared to each of the strip-shaped dense regions.

2. The composite sheet according to claim 1, wherein thermoplastic fibers that have been partially stretched have a smaller average fiber diameter than that of the thermoplastic fibers that have not been partially stretched,
a region comprising more thermoplastic fibers that have been partially stretched is the strip-shaped non-dense region, and
a region comprising more thermoplastic fibers that have not been partially stretched is the strip-shaped dense region.

3. The composite sheet according to claim 1, wherein the stretchable nonwoven fabric in an extended state is laminated on the non-stretchable sheet.

4. The composite sheet according to claim 1, wherein the average peel strength thereof, in a case where a weight weighing 40 g/cm² is placed on two of the composite sheets overlapped such that the respective surfaces of the stretchable nonwoven fabrics face each other and are left for one week at a room temperature of 50 degrees C. and a humidity of 60%, is not more than 0.15 N/50 mm.

5. An absorbent article comprising:

an absorbent body; and the composite sheet according to claim 1.

6. The composite sheet according to claim 1, wherein the adhesive portion bonds the stretchable nonwoven fabric to the non-stretchable sheet with adhesives with the stretchable nonwoven fabric extended.

7. The composite sheet according to claim 6, wherein a basis weight of the adhesives is 0.5 to 15 g/m$^2$.

* * * * *